United States Patent
Ingram, Jr. et al.

(10) Patent No.: US 8,558,884 B2
(45) Date of Patent: Oct. 15, 2013

(54) IN-SCENE DETERMINATION OF AEROSOL PARAMETERS FROM IMAGERY

(75) Inventors: Paul M. Ingram, Jr., Dallas, TX (US); Joseph C. Landry, Dallas, TX (US)

(73) Assignee: Raytheon Company, Waltham, MA (US)

( * ) Notice: Subject to any disclaimer, the term of this patent is extended or adjusted under 35 U.S.C. 154(b) by 314 days.

(21) Appl. No.: 13/100,878

(22) Filed: May 4, 2011

(65) Prior Publication Data
US 2012/0281085 A1    Nov. 8, 2012

(51) Int. Cl.
*H04N 7/18* (2006.01)
(52) U.S. Cl.
USPC .................................................. 348/135
(58) Field of Classification Search
USPC .................................................. 348/135
See application file for complete search history.

(56) References Cited

U.S. PATENT DOCUMENTS

| 2002/0096622 A1* | 7/2002 | Adler-Golden et al. ... 250/208.1 |
| 2002/0116135 A1* | 8/2002 | Pasika et al. .................... 702/21 |
| 2009/0297021 A1 | 12/2009 | Islam et al. |
| 2010/0133488 A1 | 6/2010 | Giakos |
| 2012/0035884 A1 | 2/2012 | Ingram et al. |
| 2012/0035900 A1 | 2/2012 | Ingram et al. |

OTHER PUBLICATIONS

"Iterative Retrieval of Surface Emissivity and Temperature for a Hyperspectral Sensor," Christoph A. Borel, submitted to the proceedings for the First JPL Workshop on Remote Sensing of Land Surface Emissivity, May 6-8, 1997 (8 pages).
"An Atmospheric Correction Algorithm for Hyperspectral Imagery," Sanders, Lee C.; Doctoral Dissertation, Rochester Institute of Technology, 1999 (188 pages).
"Algorithm for Remote Sensing of Tropospheric Aerosol From MODIS: Collection 5," Remer, et al. Algorithm Theoretical Basis Document, http://modis.gsfc.nasa.gov/data/atbd/atmos_atbd.php, date unknown (87 pages).
"A Simplified Approach to Radiometric Vicarious Calibration," Ryan, Robert E., date unknown, (1 page).
"The emperical line method for the atmospheric correction of IKONOS imagery," Karpouzli, E. et al., International Journal of Remote Sensing, ISSN1366-5901, copyright 2003 (8 pages).
U.S. Appl. No. 12/851,991, filed Aug. 6, 2010, entitled "Remote Identification of Non-Lambertian Materials," (89 pages).
U.S. Appl. No. 12/851,844, filed Aug. 6, 2010, entitled "Remote Material Identification Process Performance Prediction Tool," (37 pages).
"A Review of Reflectance Nomenclature Used in Remote Sensing," Carol J. Bruegge, et al., dated Jan. 7, 2000 (10 pages).
"Three-Dimensional Appearance Characterization of Diffuse Standard Reflection Materials," Andreas Hope, et al., pp. 295-304, published Apr. 29, 2010 (11 pages).

(Continued)

*Primary Examiner* — David Czekaj
*Assistant Examiner* — Mohammad J Rahman
(74) *Attorney, Agent, or Firm* — Schwegman, Lundberg & Woessner, P.A.

(57) ABSTRACT

A computer implemented method and apparatus estimate background reflectance, aerosol type and visibility within a multispectral imagery using the measured spectral radiance of one or more calibration targets of known reflectance and the measured radiance of the background of the target. The computer implemented method and apparatus uses predefined aerosol types, characterized by a plurality of known parameters, and the known reflectance of the one or more calibration targets, to select an aerosol that best matches the measured radiances.

22 Claims, 4 Drawing Sheets

(56) References Cited

OTHER PUBLICATIONS

"Lava Flow Identification and Aging by Means of LiDAR Intensity: the Mt. Etna Case," Francesco Mazzarini, et al., J. Geophys. Res., vol. 112, No. B2, Feb. 2007 (43 pages).
"Better Analysis of Hyperspectral Images by Correcting Reflectance Anisotropy," Eyal Ben-Dor, et al., SPIE Newsroom, copyright 2010 (3 pages).
"Impact of BRDF on Physics Based Modeling as Applied to Target Detection in Hyperspectral Imagery," Emmett J. Ientilucci, et al., Proc. of SPIE vol. 7334, copyright 2009 (12 pages).
"Pixel Identification Techniques Using Hybrid Spectral Algorithms and Physics Based Models," prepared for NGA, Rochester Institute of Technology, College of Science, Center for Imaging Science, Digital Imaging and Remote Sensing Laboratory, Rochester, New York, US, Dec. 2009 (9 pages).
"Optical Remote Sensing of Benthic Habitats and Bathymetry in Coastal Environments at Lee Stocking Island, Bahamas: A Comparitive Spectral Classification Approach," Eric M. Louchard, et al., pp. 511-521, dated Oct. 1, 2001 (11 pages).
"Models and Methods for Automated Material Identification in Hyperspectral Imagery Acquired Under Unknown Illumination and Atmospheric Conditions," Glenn Healey, et al., IEEE Transactions on Geoscience and Remote Sensing, vol. 37, No. 6, Nov. 1999, pp. 2706-2717 (12 pages).
"Hyperspectral Image Processing for Automatic Target Detection Applications," Dimitris Manolakis, et al., Lincoln Laboratory Journal, vol. 14, No. 1, dated 2003, pp. 79-116 (38 pages).
"Introduction to Hyperspectral Imaging," Randall B. Smith, MicroImages, Inc., dated Jul. 14, 2006 (24 pages).
"Imaging Spectrometry of Urban Materials," Dar A. Roberts, et al., dated Mar. 2004 (31 pages).
"Tensor Methods for Hyperspectral Data Analysis: A Space Object Material Identification Study," Qiang Zhang, et al., Optical Society of America, copyright 2008 (46 pages).
"Measurement and Statistical Modeling of BRDF of Various Samples," Hanlu Zhang, et al., Optica Applicata, vol. XL, No. 1, 2010, pp. 197-208 (12 pages).
"Spectral Imaging for Remote Sensing," Gary A. Shaw, et al., Lincoln Laboratory Journal, vol. 14, No. 1, 2003, pp. 3-28 (26 pages).
"Bidirectional Reflectance Distribution Function and Hemispherical Reflectance of JSC Mars-1," Georgi T. Georgiev, et al., Society of Photo-Optical Instrumentation Engineers, copyright 2002, pp. 165-175 (11 pages).
"Shadow-Insensitive Material Detection/Classification with Atmospherically Corrected Hyperspectral Imagery," Steven M. Adler-Golden, et al., SPIE, 2000, vol. 4381, Algorithms for Multispectral, Hyperspectral and Ultraspectral VII, pp. 460-469, (10 pages).
"Target Detection and Classification at Kernel Blitz 1997 Using Spectral Imagery," Jeffrey D. Sanders, Thesis, Naval Postgraduate School, Dec. 1998 (115 pages).
"Development of Global Aerosol Models Using Cluster Analysis of Aerosol Robotic Network (AERONET) Measurements," Ali H. Omar, et al., published Mar. 1, 2005 (14 pages).
"In-Scene Determination of Aerosol Parameters From Imagery", U.S. Appl. No. 13/100,878, filed May 4, 2011, 30 pgs.
Kerekes, John, et al., "Characterization of Material Reflectance Variation Through Measurement and Simulation", Proc. of SPIE vol. 7695, (May 2010), 11 pgs.
Strackerjan, Kristin, et al., "Modeling the Spectral Effects of Water and Soil as Surface Contaminants in a High Resolution Optical Image Simulation", IEEE, (2006), 3757-3760.

* cited by examiner

IN-SCENE DETERMINATION OF AEROSOL PARAMETERS FROM IMAGERY

The U.S. government may have certain rights in this invention pursuant to its funding under contract No. 2004-K724300-000.

TECHNICAL FIELD

The invention relates generally to methods and systems for determining parameters of aerosols present within the atmosphere from acquired imagery.

BACKGROUND

An aerosol is a suspension of fine solid particles or liquid droplets in a gas. Aerosols that are present in the earth's atmosphere affect propagation of electromagnetic radiation in at least the visible and near infrared parts of the spectrum. Many uses of images taken by remote sensors require that the effects of atmospheric scattering and absorption be taken into account so that the true radiance leaving the ground can be determined.

There are a number of applications for methods of determining the characteristics of the aerosols at a particular location, one of which is remote material identification. Remote material identification processes use specially programmed computers to analyze and determine from images of a remote object the material from which its surface is made. The determination is based in part on the spectral radiance of the object's surface within the image. The target's spectral reflectance is estimated from the measured spectral radiance, using a model of the illumination of the target surface by the sun and atmosphere. Once the spectral reflectance of the target material is determined, it can be compared with the known spectral reflectance of different materials for a match.

Because aerosol in the atmosphere will affect the propagation of the electromagnetic radiation, it should be taken into account by the model when determining the reflectance of the target material. Examples of parameters typically used to characterize aerosols include extinction coefficient, absorption coefficient (or equivalently by a single scatter albedo), and asymmetry factor. Background is characterized by a single band-effective reflectance in each sensor band.

One approach to inferring aerosol properties from multi-spectral images is to assume an aerosol type, and then attempt to characterize the amount of that aerosol present in the atmosphere. For example, the Regression Intersection Method for Aerosol Correction (RIMAC) assumes an aerosol type and then proceeds to use image data to estimate the visibility, which is directly related to aerosol concentration. See Sanders, "An Atmospheric Correction Algorithm for Hyperspectral Imagery", Doctoral Dissertation, Rochester Institute of Technology, 1999. In another prior art approach, the land aerosol retrieval algorithm for the Moderate Resolution Imaging Spectroradiometer (MODIS) assumes a mixture of two types of aerosols (a coarse aerosol and a fine aerosol), determines the mixing ratio, and then estimates the aerosol optical depth, which is directly related to aerosol concentration. See, Remer et al, "Algorithm For Remote Sensing Of Tropospheric Aerosol From MODIS: Collection 5", Algorithm Theoretical Basis Document, http://modis.gsfc.nasa.gov/data/atbd/atmos_atbd.php.

An in-scene method for estimating target reflectance from spectral reflective imagery, called Empirical Line Method (ELM), takes into account atmospheric conditions. However, it requires the use of at least two, and preferably three or more, calibration references of known reflectance be present in the scene.

SUMMARY

The method and apparatus described below estimate background reflectance and visibility within one or more multi-spectral images using the measured spectral radiance of one or more calibration targets of known reflectance and the measured radiance of the background of the target.

One exemplary embodiment of a computer implemented method and apparatus uses predefined aerosol types, characterized by a set of two or more known parameters, and the known reflectance of the one or more calibration targets, to select an aerosol that best matches the measured radiances. It is capable of estimating visibility and background reflectance within imagery with just one calibration reference, thereby simplifying the process and improving the chances of success as compared to other in-scene methods. An unregularized method for estimating a set of parameters per band from the continuum of possible values would require the presence of at least a number of calibration references in the scene equal to the number of parameters. It is difficult for a user to be able to identify this many calibration references in a typical scene.

DETAILED DESCRIPTION

In the following description, like numbers refer to like elements.

Figure 1:
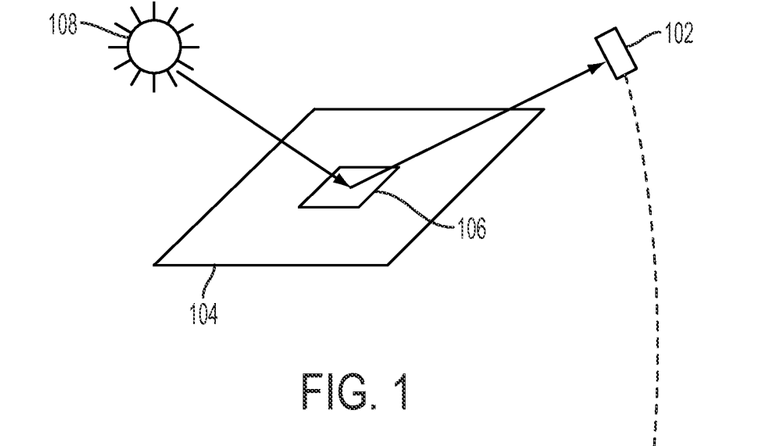
FIG. 1 is a schematic illustration of an area containing a target of interest, being illuminated by the sun and imaged by a passive remote sensor.

Referring to FIG. 1, which is a schematic illustration of the acquisition of an image, sensor 102 acquires imagery of at least a portion of an area of land 104 containing one or more targets of interest, for example, target 106. In this example, the sun 108 is illuminating the scene. However, other sources of illumination of the target are possible, including, for example, other man-made sources of illumination.

In this example, sensor 102 is a passive electro-optical sensor. The sensor is either multispectral or hyperspectral. Aircraft or satellites, for example, carry the sensor. However, the sensor could be placed anywhere that affords a view of the area containing a target of interest. Images acquired from the sensor are stored on computer readable media for further processing. Images may be acquired using more than one sensor. The image data is delivered, either by transmitting it or by transporting it on physical media, to an image processing facility (not shown) for reconstruction if necessary) and further processing. The same or a different facility can perform the methods described herein. The facility includes one or more specially programmed computers and storage devices.

Once an image is acquired, parameters describing aerosol present in the atmosphere and background reflectance in an image can be estimated from it. Aerosol parameters and background reflectance in an image are used, for example, to model the illumination of the target by the sun and atmosphere as a function of zenith and azimuth angles as part of an automated remote material identification process. Estimated aerosol parameters are also useful for other purposes, as part of other types of methods or apparatus.

Figure 2:
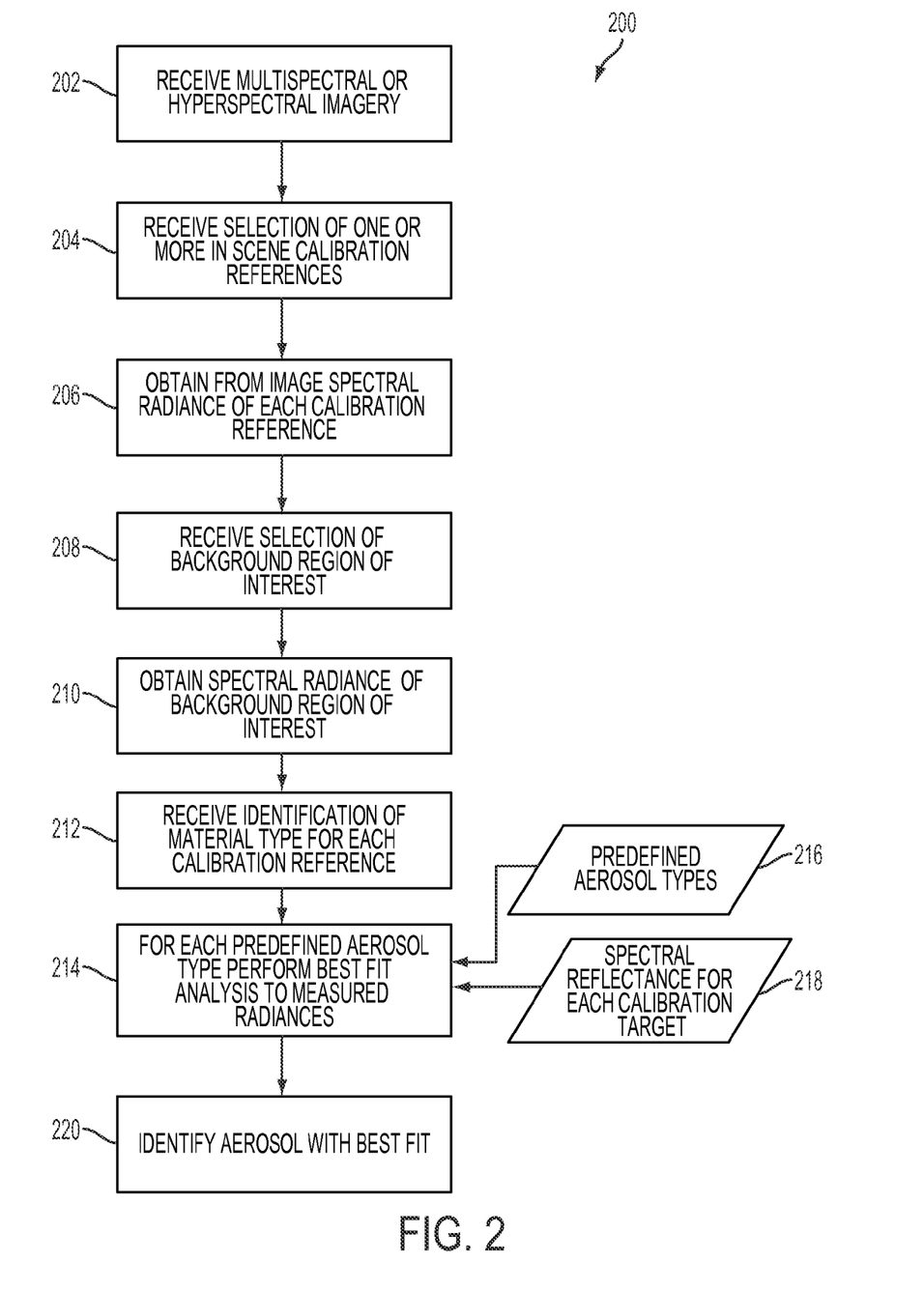
FIG. 2 is a flow diagram of a computer-implemented method for estimating aerosol parameters using remotely sensed imagery.

Referring to FIG. 2, represented by the flow chart 200 is an example of, or a representative embodiment for, a computer implemented method or process for inferring aerosol parameters from the radiance of one or more calibration references present in one or more images of the same scene, and the radiance of the background of the one or more calibration references, using the known reflectance characteristics of the calibration reference and the predetermined characteristics of a set of two or more of predefined aerosol types. If multiple images are used, they should be acquired closely enough in time to ensure that the aerosol type and amount are the same for all the images. A calibration reference is an object having a surface made from a known material. The reflectance of the known material is known from measurements previously made of the material. It is stored, for example, in a database or file on a computing system or provided by the user. The imagery is, in the embodiments described below, radiometrically calibrated, and includes at least two spectral bands. Examples of such imagery include multispectral (MS) and hyperspectral (HS) imagery. Spectral radiance measurements of the one or more calibration references and the background are obtained from the image data.

The representative embodiment of the method estimates three parameters for aerosol indicative of visibility, namely an extinction coefficient, an absorption coefficient (or equivalently by a single scatter albedo), and an asymmetry parameter. Background reflectance is characterized by a single band-effective reflectance in each sensor band, which the representative method estimates.

In the representative embodiment, the user indicates, using either computer interfaces or in a configuration data file stored on the computer, one or more in-scene targets that serve as calibration references with the following properties. It is preferred that each calibration target, which is a visible surface of an object in the scene, is composed of a Lambertian or near Lambertian material which is horizontal, and whose spectral reflectance within the spectral range of the sensor is known. If more than one calibration target is indicated, it is preferred, for best results, that all of the calibration targets have a common background within the scene, are at approximately the same elevation and fully illuminated. The atmospheric conditions should also be the same over each target.

At step 202, imagery is received by the computer and stored in memory. The imagery is communicated to the computer by transporting the imagery on computer readable physical media, transmitting the imagery using electrical or optical signals, or by combination of communication modes.

The specially programmed computer receives from a user at step 204 a selection of one or more in-scene calibration references. In one embodiment, selection takes the form of a user delineating to the computer, using an input device and a display, a target region of interest (ROI) within the image, which constitutes a grouping of pixels, for each calibration reference. Alternately, the selection of the target is done automatically by the specially programmed computing system.

At step 206 the specially programmed computer obtains, for each calibration target, a measurement of spectral radiance from the indicated ROI in the imagery.

The computer determines at step 210, using the image and stores in computer memory the mean radiance of the background common to all the calibration targets, by receiving at step 208 from the user a selection of a background region of interest that surrounds, but excludes, the calibration targets and retrieving its mean spectral radiance from the image.

At step 212 the specially programmed computer receives an indication from the user for each calibration target of the type of material of which it is made, and looks up the reflectance spectrum of the target material stored in a file or database. For example, it can be stored in a database or other type of file stored in computer memory. This step can be performed at the time the calibration target is identified.

As indicated by step 214, the process then determines, for each of a plurality of aerosol types, a best fit of the aerosol to the measured radiances of the one or more calibration targets and their background, obtained from the images at steps 206 and 212, using the known reflectance of each of the calibration targets. In one embodiment, the filtering process may include a least square process. One example of a least square process is a chi-square fitting process. The aerosol types 216 and the spectral reflectance 218 for the material from which each of the calibration targets is made are stored in one or more databases or files accessible by the process. Accessible databases or files can be stored, for example, on the specially programmed computer, in memory or in storage devices attached to the computer, or by a remote computer or device with which the computer may communicate. A user can, optionally, provide or define the aerosol types to the process as input to the specially programmed computer. The user at least provides or identifies the material from which each of the calibration reference is composed of. The spectral reflectance for the material for each of the calibration targets is looked up in a database or file accessible by a specially programmed computer executing the process. Alternately, or in addition, the process may receive the spectral reflectance for the calibration target as an input from a user.

Each aerosol type is predefined using, in the exemplary embodiment, the parameters of extinction coefficient, an absorption coefficient (or equivalently by a single scatter albedo) and an asymmetry factor. A cluster analysis study of AERONET data (Aerosol Robotic Network) has shown that there are, effectively, six (6) types of aerosols. See, Omar, et al., "Development of global aerosol models using cluster of Aerosol Robotic Network (AERONET) measurements", Journal of Geophysical Research, vol. 110, March 2005. These aerosol types may be used as the predefined aerosol types. Parameters at each of three wavelengths for these aerosol types are given in Table 1. Additional aerosol types could be defined and used in the process. A fewer number of aerosol types could also be defined and selected for use in the process.

TABLE 1

|  | Type 1: Desert Dust | Type 2: Biomass Burning | Type 3: Rural (Background) | Type 4: Industrial Pollution | Type 5: Polluted Marine | Type 6: Dirty Pollution |
| --- | --- | --- | --- | --- | --- | --- |
| Single scattering albedo @ 441 nm | 0.923452 | 0.841479 | 0.906909 | 0.937582 | 0.931900 | 0.752894 |
| Single scattering albedo @ 673 nm | 0.927965 | 0.800305 | 0.877481 | 0.921652 | 0.925049 | 0.717840 |
| Single scattering albedo @ 873 nm | 0.926163 | 0.765592 | 0.853717 | 0.905481 | 0.917595 | 0.667695 |
| Single scattering albedo @ 1022 nm | 0.927608 | 0.745263 | 0.846585 | 0.895503 | 0.910512 | 0.633196 |
| Extinction coefficient @ 441 nm | 0.406217 | 0.348215 | 0.067341 | 0.370811 | 0.194477 | 0.180477 |
| Extinction coefficient @ 673 nm | 0.326517 | 0.190405 | 0.035950 | 0.190634 | 0.139910 | 0.100125 |
| Extinction coefficient @ 873 nm | 0.291773 | 0.132512 | 0.025993 | 0.125879 | 0.114592 | 0.071986 |
| Extinction coefficient @ 1022 nm | 0.280223 | 0.111652 | 0.022831 | 0.101389 | 0.102874 | 0.063466 |
| Asymmetry factor @ 441 nm | 0.692541 | 0.664340 | 0.649253 | 0.694172 | 0.740076 | 0.679427 |
| Asymmetry factor @ 673 nm | 0.667937 | 0.603481 | 0.580048 | 0.611590 | 0.710529 | 0.594261 |
| Asymmetry factor @ 873 nm | 0.672450 | 0.582214 | 0.571153 | 0.574028 | 0.715632 | 0.571046 |
| Asymmetry factor @ 1022 nm | 0.673933 | 0.579726 | 0.574551 | 0.562794 | 0.714759 | 0.565743 |

Finally, at step 220, the computer-implemented process identifies an aerosol type with a best fit to the observed radiances in the imagery.

Figure 3:
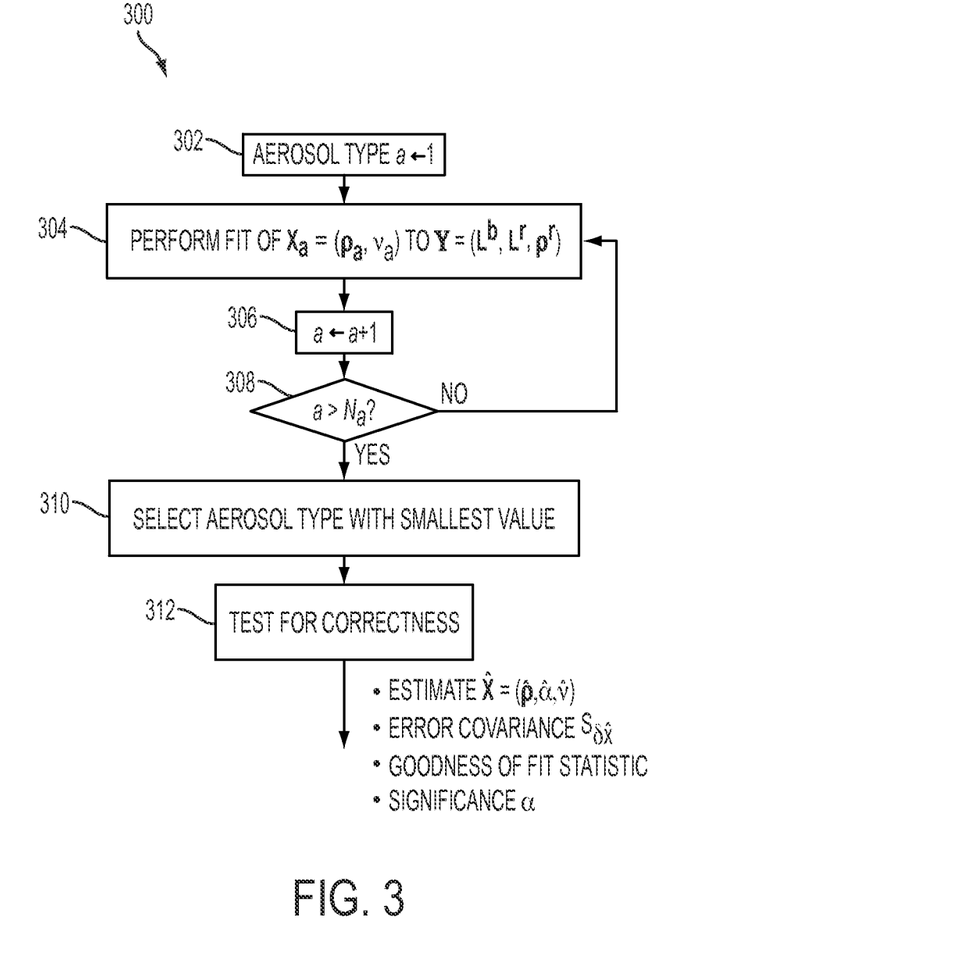
FIG. 3 is a schematic illustration of basics steps of representative example of a computer-implemented method for performing, as part of the method of FIG. 2, a best fit analysis for each of a plurality of predetermined aerosol types and selecting the aerosol with best fit.

Turning to FIG. 3, flow chart 300 represents the basic steps of an example of a computer-implemented process for performing step 214 of FIG. 2. The process assumes that the scene is cloud free and that radiance measurements, reflectance measurements, etc. have Gaussian error statistics.

In the following description of the computer-implemented process, $N_r$ represents the number of calibration references imaged by a non-polarimetric reflective MSI sensor with $N_b$ band. The number of calibration references is greater than or equal to one. The known spectral reflectance of calibration reference i is denoted by $\rho_i^r(\lambda)$, where $\lambda$ is wavelength. The measured aperture radiance of calibration reference i in band j is denoted by $L_{i,j}^{ap}$, and the measured background radiance by $L_{N_r,j}^{ap}$, where i=0, K, $N_r-1$, and j=0, K, $N_b-1$.

A state space is defined consisting of vectors $X=(\rho,\alpha,\nu)$, where $\rho=(\rho_0,K,\rho_{N_b-1})$ is the gray body equivalent background reflectance, assumed to be the same for all targets, $\alpha$ is the aerosol type and $\nu$ is the visibility. State space therefore has dimension $N_b+2$. A measurement space is defined, consisting of vectors $(L_0^{ap},K,L_{N_r}^{ap})$, where each $L_i^{ap}$ is itself a vector of length $N_b$ consisting of the measured radiances of calibration reference i in each band plus the measured background radiance. Measurement space therefore has dimension $N_b \cdot (N_r+1)$.

As indicated by steps 302, 304, 306 and 308, for each aerosol type a, a least square fit of the state $X=(\rho,\alpha,\nu)$ to the radiance measurement and reflectance of each of the one or more calibration references and the measured radiance of the background, represented by measurement $Y=(L^b,L^r,\rho^r)$, performed. At step 310, a final state estimate $\hat{X}=(\hat{\rho},\hat{\alpha},\hat{\nu})$ is then selected. One example of a least square fit process is a chi-square fitting process. One embodiment of a chi-square process for performing steps 304 and 310 is described in connection with FIG. 4. Once the aerosol type with the smallest least square value is selected, final state estimate with the selected aerosol is tested for correctness at step 312. One implementation for this test is described below.

Figure 4:
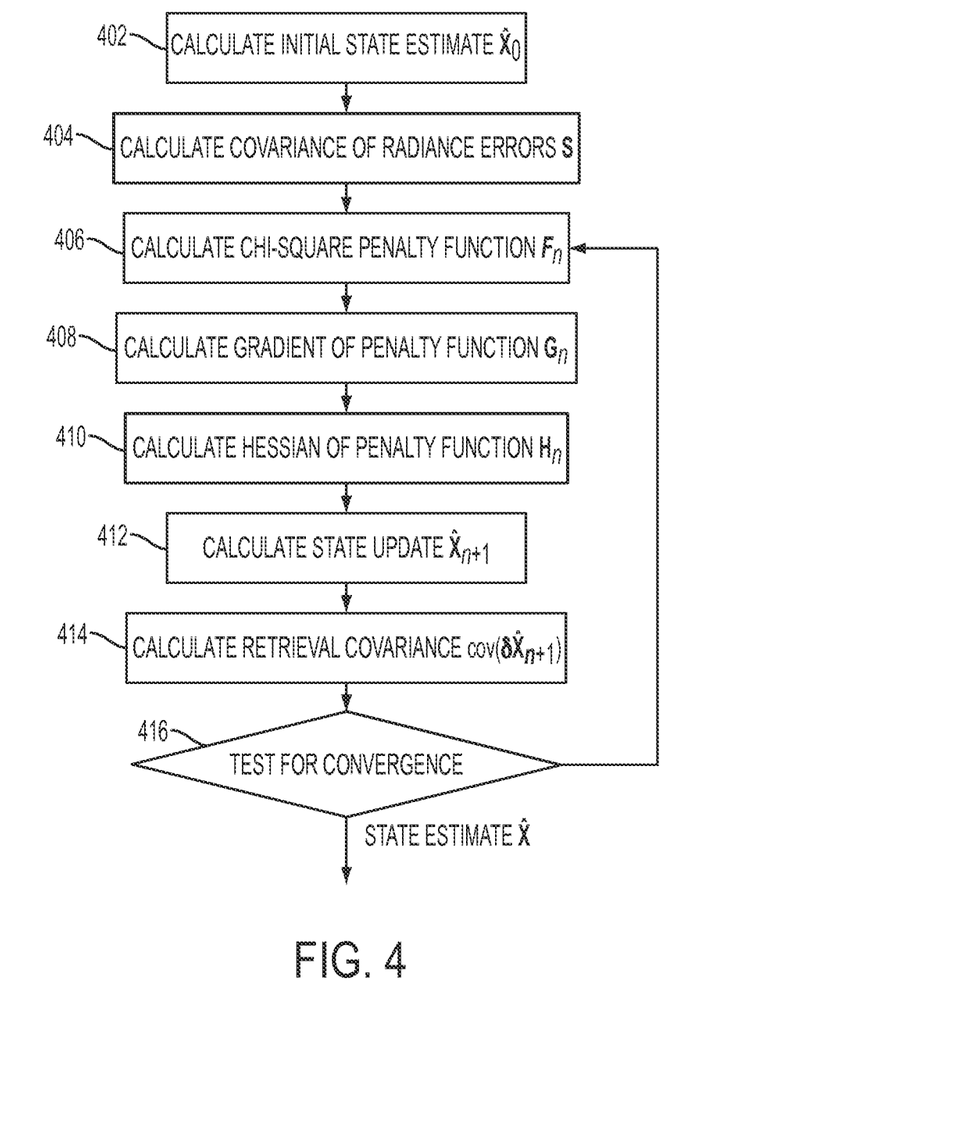
FIG. 4 is schematic illustration of a representative example of a method for estimating, as part of the computer implemented method of FIG. 3, the amount of an assumed aerosol type that is present in a scene imaged by a remote sensor.

Referring now to FIG. 4, for given aerosol type $\alpha$, flow chart 400 describes a computer implemented process for performing a chi-square fit of the state $X=(\rho,\alpha,\nu)$ to measurements $Y=(L^b,L^r,\rho^r)$. Since the aerosol type is fixed, $\alpha$ is dropped from the state and the state is written as $X=(\rho,\nu)$.

The chi-square fitting process involves a forward model function, denoted by L, which maps state space to measurement space. So L consists of $N_b \cdot (N_r+1)$ functions denoted $L_{i,j}: R^{N_b+1} \to R$ for i=0, K, $N_r$ and j=0, K, $N_b-1$. Each $L_{i,j}$ is calculated as follows. Given an aerosol type $\alpha$ and a visibility $\nu$, calculate the following spectral background-independent path (BIP) terms:

$L^{AS}(\lambda)$: Solar photons that are scattered into the sensor's field of view via single or multiple scatter events within the atmosphere without ever reaching the target or background.

$L^{DSR}(\lambda)$: Solar photons that pass directly through the atmosphere to a 100% reflectance Lambertian target, reflect off the target, and propagate directly through the atmosphere to the sensor. Light for this path term is attenuated by absorption and by light scattering out of the path, but no radiance is scattered into the path. This path does not involve any interaction with the background.

$L^{SSR}(\lambda)$: Solar photons that are scattered by the atmosphere onto a 100% reflectance Lambertian target, reflect off the target, and propagate directly through the atmosphere to the sensor. This path term does not involve any interactions with the background.

$L^{BDSR}(\lambda)$: Solar photons that are directly transmitted to a 100% reflectance Lambertian background, reflect off the background once, and then scatter into the field of view of the sensor.

$L^{BSSR}(\lambda)$: Solar photons that are scattered by the atmosphere at least once, reflect off a 100% reflectance Lambertian background once, and then scatter into the field of view of the sensor.

$S(\lambda)$: Spherical albedo of the bottom of the atmosphere, which can be thought of as a reflection coefficient of the atmosphere.

Denote $L^{SR}=L^{DSR}+L^{SSR}$ and $L^{BSR}=L^{BDSR}+L^{BSSR}$. Denote the relative spectral response function of the sensor in band j by $R_j(\lambda)$. Then $L_{i,j}(\rho_j,\nu;\rho_i^r)$ is defined by:

$$L_{i,j}(\rho_j, \nu) = \begin{cases} \int \left[ L^{AS} + \frac{\rho_i^r}{1-\rho_j S} L^{SR} + \frac{\rho_j}{1-\rho_j S} L^{BSR} \right] R_j(\lambda) d\lambda & i=0, K, N_r-1 \\ \int \left[ L^{AS} + \frac{\rho_j}{1-\rho_j S} (L^{SR} + L^{BSR}) \right] R_j(\lambda) d\lambda & i=N_r \end{cases} \quad (1)$$

The residual $\delta L$ is the vector in measurement space defined by:

$$\delta L(\rho, \nu) = L(\rho, \nu) - L^{ap} \quad (2)$$

At step 402, an initial estimate for the state for a given aerosol type is determined. For calibration target i, the first equation in equation (1) gives the target radiance $L_{i,j}$ in band j as a function of the background reflectance. This equation is solved for estimates $\hat{\rho}_{i,j}$ of the background reflectance by applying Newton's method to the function F and its derivative given in equation (3). This yields $N_r$ estimates $\hat{\rho}_{i,j}$, i=0, K, $N_r-1$ in each band j=0, K, $N_b-1$. The spectral BIP terms are computed from weather data describing conditions at the target when the image was acquired, including the aerosol type and visibility.

$$F(\hat{\rho}_{i,j}) = \quad (3)$$

$$\int \left[ L^{AS}(\lambda) + \frac{\rho_i^r(\lambda)}{1 - \hat{\rho}_{i,j} S(\lambda)} L^{SR}(\lambda) + \frac{\hat{\rho}_{i,j}}{1 - \hat{\rho}_{i,j} S(\lambda)} L^{BSR}(\lambda) \right] R_j(\lambda) d\lambda - L_{i,j}^{ap}$$

$$F'(\hat{\rho}_{i,j}) = \int \frac{\rho_i^r(\lambda) S(\lambda) L^{SR}(\lambda) + L^{BSR}(\lambda)}{[1 - \hat{\rho}_{i,j} S(\lambda)]^2} R_j(\lambda) d\lambda$$

The second equation in (1) gives the background radiance in band j as a function of the background reflectance. This equation is also solved to get an estimate of the background reflectance by applying Newton's method to the function F and its derivative given in equation (4). This yields an additional estimate $\hat{\rho}_{N_r, j}$ in each band.

$$F(\hat{\rho}_{N_r, j}) = \quad (4)$$

$$\int \left[ L^{AS}(\lambda) + \frac{\hat{\rho}_{N_r, j}}{1 - \hat{\rho}_{N_r, j} S(\lambda)} [L^{SR}(\lambda) + L^{BSR}(\lambda)] \right] R_j(\lambda) d\lambda - L_{N_r, j}^{ap}$$

$$F'(\hat{\rho}_{N_r, j}) = \int \frac{L^{SR}(\lambda) + L^{BSR}(\lambda)}{[1 - \hat{\rho}_{N_r, j} S(\lambda)]^2} R_j(\lambda) d\lambda$$

The $N_r+1$ values $\hat{\rho}_{i,j}$, i=0, K, $N_r$, are averaged as in equation (5) to give the initial estimate $\hat{\rho}_j$ of the background reflectance in band j:

$$\hat{\rho}_j = \frac{1}{N_r + 1} \sum_{i=0}^{N_r} \hat{\rho}_{i,j} \quad (5)$$

The $N_b$ values in equation (5) give the initial estimate of the background reflectance, denoted $\hat{\rho}_0$. The initial estimate of the visibility $\hat{\nu}_0$ is taken from an estimate of weather conditions over the target at the time the image was acquired. The initial estimate of the state vector is now given by $\hat{X}_0 = (\hat{\rho}_0, \hat{\nu}_0)$.

At step 404, covariance of radiance errors are determined. The chi-square fitting process requires calculating the covariance of errors in $L^{ap}$, which is an $[N_b \cdot (N_r+1)] \times [N_b \cdot (N_r+1)]$ matrix denoted by S. The covariance of radiance measurement errors will be assumed to be diagonal, i.e. measurement errors are assumed to be uncorrelated between bands, and between calibration targets and the background. This assumption could be eliminated if information about error correlations is available. S therefore has the structure shown in equation (6), where $S_i$ is the $N_b \times N_b$ diagonal covariance matrix for $L_i^{ap}$.

$$S = \begin{bmatrix} S_0 & & \\ & O & \\ & & S_{N_r} \end{bmatrix} \quad (6)$$

Each $S_i$ is computed from $L_i^{ap}$ in accordance with equation (7), where the constant $\sigma_j^{cal}$ is the relative measurement accuracy in band j for the sensor. In practice, $\sigma_j^{cal}$ is taken to be a fixed percentage, the same in all bands, and the standard deviation of the radiance measurement errors is then given by $\sigma_{\delta L_j} = \sigma_j^{cal} L$.

$$S_i = \begin{bmatrix} (\sigma_0^{cal} L_{i,0}^{ap})^2 & & \\ & O & \\ & & (\sigma_{N_b-1}^{cal} L_{i,N_b-1}^{ap})^2 \end{bmatrix} \quad (7)$$

At step 406, a chi-square penalty function is determined. The estimated state $\hat{X} = (\hat{\rho}, \hat{\nu})$ is calculated as the state that minimizes a penalty (or objective) function denoted by F(X). This function is non-linear, so minimization is performed iteratively, starting with the initial estimate $X_0$, and continuing with updated estimates $X_{n+1}$. Since the calculation of $F(X_n)$ does not depend on n, the subscript will be dropped. This convention also applies to the calculation of the gradient G and the hessian H described in connection with steps 408 and 410, respectively.

The form of F(X) is defined in equation (8). Assuming that the correct aerosol type has been selected and that errors are normally distributed, F is the chi-square statistic of $\delta L$. F can be used in a chi-square test to measure how well the solution fits the data, and to reject the solution if it fails the test. This will be described below in connection with step 312 of FIG. 3.

$$F(\rho, \nu) = \delta L(\rho, \nu)^t \cdot S^{-1} \cdot \delta L(\rho, \nu) \quad (8)$$

$$= [\delta L_0^t \quad L \quad \delta L_{N_r}^t] \begin{bmatrix} S_0^{-1} & & \\ & O & \\ & & S_{N_r}^{-1} \end{bmatrix} \begin{bmatrix} \delta L_0 \\ M \\ \delta L_{N_r} \end{bmatrix}$$

$$= \sum_{i=0}^{N_r} \delta L_i^t \cdot S_i^{-1} \cdot \delta L_i$$

$$= \sum_{i=0}^{N_r} \sum_{j=0}^{N_b - 1} \left( \frac{\delta L_{i,j}}{\sigma_{\delta L_{i,j}}} \right)^2$$

At step 408, the gradient of the penalty function is calculated by the computer implemented process.

The solution $\hat{X} = (\hat{\rho}, \hat{\nu})$ is found by minimizing F. This is accomplished by finding a zero of the $(N_b+1)$-vector field $G = \nabla F$. The first $N_b$ components of G are given by:

$$G_m = \frac{\partial F}{\partial \rho_m} \quad (9)$$

-continued $$= 2\sum_{i=0}^{N_r}\sum_{j=0}^{N_b-1}\frac{1}{\sigma_{L_{i,j}}^2}\frac{\partial L_{i,j}}{\partial \rho_m}\delta L_{i,j}$$

In equation (9), $L_{i,j}$ depends only on $\rho_j$, so $\partial L_{i,j}/\partial \rho_m$ is zero unless $j=m$. Equation (9) therefore simplifies to equation (10), where $\delta_{i,j}$ is the Kronecker delta function:

$$G_m = 2\sum_{i=0}^{N_r}\sum_{j=0}^{N_b-1}\frac{1}{\sigma_{\delta L_{i,j}}^2}\frac{\partial L_{i,j}}{\partial \rho_m}\delta_{m,j}\delta L_{i,j} \qquad (10)$$

$$= 2\sum_{i=0}^{N_r}\frac{1}{\sigma_{L_{i,m}}^2}\frac{\partial L_{i,m}}{\partial \rho_m}\delta L_{i,m}$$

$$m = 0, K, N_b - 1$$

The last component of G is given by equation (11). It is evaluated via perturbation because F cannot be written as a closed form function of $\nu$.

$$G_{N_b} = \frac{\partial F}{\partial \nu} \qquad (11)$$

$$= \frac{F(\nu + \delta\nu) - F(\nu - \delta\nu)}{2\delta\nu}$$

Equation (12) gives an expression for the derivatives $\partial L/\partial \rho$ found in equation (10). This equation takes advantage of the background-independent path term formalism by expressing the derivative in terms of quantities already computed.

$$\frac{\partial L_{i,m}}{\partial \rho_m} = \int \frac{\rho_i^r(\lambda)S(\lambda)L^{SR}(\lambda) + L^{BSR}(\lambda)}{[1-\hat{\rho}_m S(\lambda)]^2}R_m(\lambda)d\lambda \qquad (12)$$

At step 410, the computer implemented process determines the Hessian of the penalty function. Finding a zero of G amounts to solving the system of equations (13):

$$G_m(\rho,\nu)=0 \quad m=0,K,N_b \qquad (13)$$

The gradient G given by the left hand side of equations (13) is typically non-zero when evaluated at the initial estimate $(\hat{\rho}_0,\nu_0)$ of the state vector. To find a zero of G, the Newton-Raphson method is used, which involves computing the Hessian H of F given in equation (14):

$$H = \begin{bmatrix} \frac{\partial^2 F}{\partial \rho_0^2} & L & \frac{\partial^2 F}{\partial \rho_0 \partial \rho_{N_b-1}} & \frac{\partial^2 F}{\partial \rho_0 \partial \nu} \\ M & O & M & M \\ \frac{\partial^2 F}{\partial \rho_{N_b-1}\partial \rho_0} & L & \frac{\partial^2 F}{\partial \rho_{N_b-1}^2} & \frac{\partial^2 F}{\partial \rho_{N_b-1}\partial \nu} \\ \frac{\partial^2 F}{\partial \nu \partial \rho_0} & L & \frac{\partial^2 F}{\partial \nu \partial \rho_{N_b-1}} & \frac{\partial^2 F}{\partial \nu^2} \end{bmatrix} \qquad (14)$$

Equation (15) gives an expression for the terms $\partial^2 F/\partial\rho_m\partial\rho_n$ found in equation (14):

$$\frac{\partial^2 F}{\partial \rho_m \partial \rho_n} = \frac{\partial}{\partial \rho_m}2\sum_{i=0}^{N_r}\frac{1}{\sigma_{\delta L_{i,n}}^2}\frac{\partial L_{i,n}}{\partial \rho_n}\delta L_{i,n} \qquad (15)$$

$$= 2\sum_{i=0}^{N_r}\frac{1}{\sigma_{L_{i,n}}^2}\left\{\frac{\partial^2 L_{i,n}}{\partial \rho_m \partial \rho_n}\delta L_{i,n} + \frac{\partial L_{i,n}}{\partial \rho_n}\frac{\partial L_{i,n}}{\partial \rho_m}\right\}$$

By the same observation that was used to obtain equation (10), equation (15) simplifies to equation (16):

$$\frac{\partial^2 F}{\partial \rho_m \partial \rho_n} = \begin{cases} 2\sum_{i=0}^{N_r}\frac{1}{\sigma_{\delta L_{i,n}}^2}\left\{\frac{\partial^2 L_{i,n}}{\partial \rho_n^2}\delta L_{i,n} + \left(\frac{\partial L_{i,n}}{\partial \rho_n}\right)^2\right\} & m=n \\ 0 & m\neq n \end{cases} \qquad (16)$$

Equation (17) gives an expression for the term $\partial^2 F/\partial\nu\partial\rho_m$ found in equation (14):

$$\frac{\partial^2 F}{\partial \nu \partial \rho_m} \approx \frac{\frac{\partial F}{\partial \rho_m}(\nu+\delta\nu)-\frac{\partial F}{\partial \rho_m}(\nu-\delta\nu)}{2\delta\nu} \qquad (17)$$

Equation (18) gives an expression for the term $\partial^2 F/\partial\nu^2$ found in equation (14):

$$\frac{\partial^2 F}{\partial \nu^2} = \frac{F(\nu+\delta\nu)+F(\nu-\delta\nu)-2F(\nu)}{\delta\nu^2} \qquad (18)$$

Equation (19) gives an expression for the term $\partial^2 L_{i,n}/\partial\rho_n^2$ found in equation (14):

$$\frac{\partial^2 L_{i,n}}{\partial \rho_n^2} = \int \frac{\rho_i^r(\lambda)L^{SR}(\lambda)+L^{BSR}(\lambda)}{[1-\rho_n S(\lambda)]^3}S(\lambda)R_n(\lambda)d\lambda \qquad (19)$$

Having calculated H at step 410, an updated estimate of the state is calculated at step 412. The change in the state vector $\delta\hat{X}$ is calculated using equation (20):

$$\delta\hat{X}=H^{-1}\cdot G \qquad (20)$$

A new estimate $\hat{X}_{n+1}$ is now computed from the current estimate $\hat{X}_n$ as:

$$\hat{X}_{n+1}=\hat{X}_n-\delta\hat{X} \qquad (21)$$

At step 414, the covariance of the errors in the retrieved state vector is determined according to equation (22).

$$\mathrm{cov}(\delta\hat{X}) = \left[\sum_{i=0}^{N_r}\frac{\partial L_i}{\partial X}\cdot S_i^{-1}\cdot\left(\frac{\partial L_i}{\partial X}\right)^t\right]^{-1} \qquad (22)$$

At step 416, the changes in the chi-square statistics shown in equation (23) are evaluated according to equations (23):

$$\delta\chi_c^2(\delta L)=F(\hat{X}')-F(\hat{X}) \qquad (23)$$

$$\delta\chi_x^2(\delta\hat{X})=\delta\hat{X}\cdot\mathrm{cov}(\delta\hat{X})^{-1}\cdot\delta\hat{X}$$

Steps 406 to 416 are repeated in an iterative process until the condition in equation (24) is satisfied:

$$\delta\chi^2(\delta L)<0.1 \text{ and } \delta\chi^2(\delta\hat{X})<0.1 \quad (24)$$

The process described above in steps 402 to 416 are repeated for each of $N_a$ aerosol type to obtain $N_a$ chi-square values $\chi_a$, $\alpha=1,K,N_a$. The aerosol type index $\hat\alpha$ with the smallest chi-square value is selected in accordance with equation (25):

$$\hat\alpha = \arg\min\{\chi_a^2\} \quad (25)$$

The full solution for the final estimate of the state is then $\hat{X}=(\hat\rho,\hat\alpha,\hat v)$.

Referring back to FIG. 3, once the final estimate of the state is obtained, it is tested for correctness at step 312. $N_b+2$ quantities in the state vector have been estimated from $N_b \cdot (N_r+1)$ measurements. Assuming errors are normally distributed, F should have a chi-square distribution with $N_b \cdot (N_r+1) - N_b - 2 = N_b N_r - 2$ degrees of freedom. The correctness of the solution can therefore be tested using the value of $F(\hat X)$. One computes the significance $\alpha(\hat X)$ from the cumulative chi-square distribution function P as:

$$\alpha(\hat X)=P(y:|y-\overline{\chi^2}|>|F(\hat X)-\chi^2|) \quad (26)$$

$\alpha$ is the probability of getting a worse value of $F(\hat X)$ even when $\hat X$ is a valid estimate.

A threshold $\tau$ for $\alpha$ is set, say $\tau=5\%$, and an estimate is accepted or rejected depending on the result of the test in equation (27):

$$\alpha(\hat X)\leq\tau \Rightarrow \text{accept } \hat X \quad (27)$$

$$\alpha(\hat X)>\tau \Rightarrow \text{reject } \hat X$$

If an estimate for a selected, predefined aerosol is accepted, the parameters describing the selected, predefined aerosol are chosen to be the parameters describing the aerosol present in the image.

Figure 5:
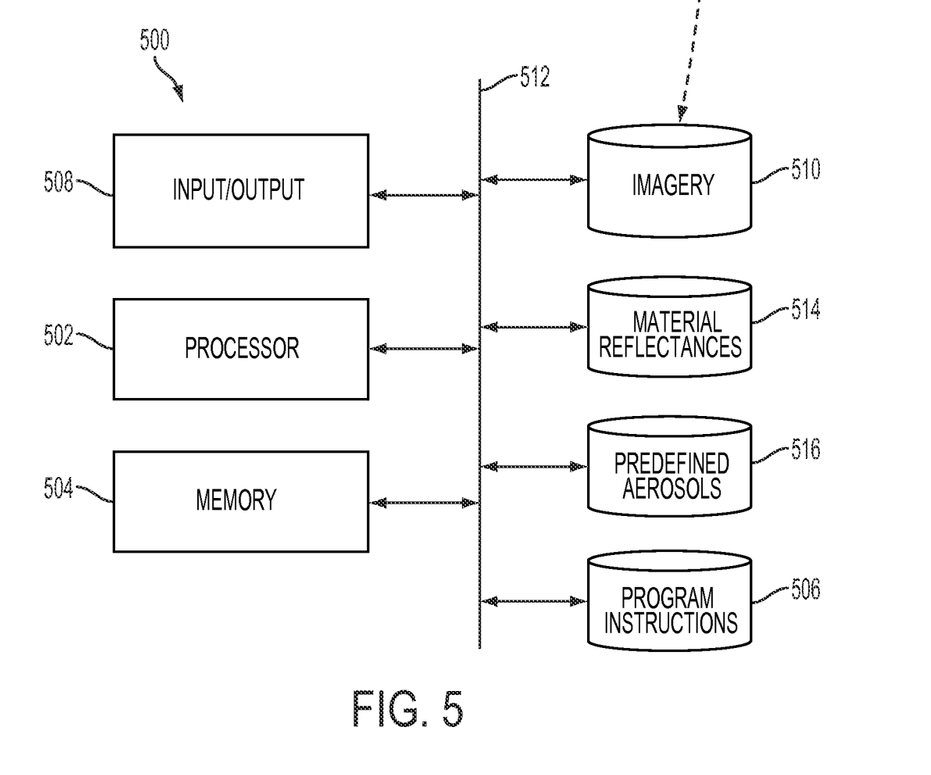
FIG. 5 illustrates a representative, specially programmed computing system for executing software for performing the computer implemented process of FIGS. 2 to 4.

FIG. 5 illustrates a representative, specially programmed computing system 500 for executing software for performing the computer implemented processes of FIGS. 2 to 4. The computer system can, for example, take the form of a personal or minicomputer, or any other device or machine with one or more processors for executing program instructions. The computing system 500 comprises one or more processors, which are represented generally by processing entity 502, and working memory 504, in which program instructions 506 are loaded for execution by processing entity 502. The processors can be general purpose, special purpose, or a combination. These instructions can also be stored or contained on any type of electronic, optical or magnetic media, as well as on transient signals, that can be read by the computing system. The instructions, which may first need to be compiled, are loaded into the memory from storage media for execution by the processor. Examples of such storage media include mass data storage and removable media. Data on which the process acts, as well as data resulting from operations of the processing entity 502, may be stored in memory 504.

The system also includes an input/output subsystem 508, which is representative of one or more subsystems through which the computing system may interact with a user or may communicate with other computing systems by transmitting information using signals. Examples of the one or more subsystems include a display, a user input device, such as a keyboard, mouse, touch pad, touch screen, or remote gesture recognition device, through which a user may interact with the program, and interfaces for communicating with other computing systems or devices. No particular computer architecture is intended by, or is to be implied from, this example. The example is intended to be representative generally of computing systems suitable for being programmed to perform these processes, and not limiting. Furthermore, the processing need not be limited to a single computing system, but could be distributed among more than one computing system. Furthermore, different programs running on computing system 500 or on multiple computing systems may execute parts of the process described by FIG. 2.

The process carried out by the computing system 500 operates on imagery stored in imagery storage system 510. Storage system 510 is intended to be representative of any type of system for storing acquired imagery. It could be a simple file system or one or more databases, for example. Imagery acquired through, for example, sensor 102 of FIG. 1 is stored in system 510. The storage system 510 is illustrated as being local, communicating over bus 512 with the processor 502 and memory 504. It could be stored on a local hard drive, for example. However, it could also be located on a mass data storage device located elsewhere on a local or wide area network, or on a remote server. Database 514 is representative of one or more databases containing predetermined or previously measured information or models for determining surface reflectance characteristics and parameters of materials for calibration references. Database 516 stores aerosol types for use by the process of FIG. 2. Each of the databases are being stored locally and communicating over bus 512 with the processor. However, each can be stored on a local or wide area network, or accessed remotely through a server. Furthermore, flat files or other structures for storing the data can be utilized. Although databases 510, 514 and 516, as well as the program instructions 506, are indicated as being stored on separate media, some are all of them can be stored on common media, for example a single hard drive of a computer. The diagram is not intended to imply any particular configuration or type of media for storing the data and program instructions.

The foregoing description is of exemplary and preferred embodiments employing at least in part certain teachings of the invention. The invention, as defined by the appended claims, is not limited to the described embodiments. Alterations and modifications to the disclosed embodiments may be made without departing from the invention as set forth in the amended claims. The meanings of the terms used in this specification are, unless expressly stated otherwise, intended to have ordinary and customary meaning and are not intended to be limited to the details of the illustrated structures or the disclosed embodiments.

What is claimed is:

1. A computer implemented method for estimating properties of aerosol present in the atmosphere of a scene from imagery taken of the scene, comprising:
   receiving with a specially programmed computer multispectral or hyperspectral imagery of the scene, from which radiance measurements in at least two spectral bands can be obtained;
   receiving with the specially programmed computer a delineation within the imagery of at least one calibration target made from a known material;
   determining from the imagery a radiance measurement for each target of the at least one calibration target in multiple spectral bands including each of at least two spectral bands having distinct wavelength ranges;
   determining from the imagery a single radiance calibration reference for a background common to each target of the at least one calibration target, the single calibration reference excluding non-background radiance measurements from the at least one calibration target;
   for each of a predefined plurality of aerosol types, each aerosol being defined by a plurality of properties, fitting with a fitting process executing on the specially programmed computer a background reflectance of the scene to radiance measurements of the at least one calibration target and the single radiance calibration reference for the background, using at least the properties of the aerosol and a predetermined spectral reflectance of the at least one calibration target in each of the multiple spectral bands; and selecting the predefined aerosol that results in the best fit, the properties of the predefined aerosol being estimates for the properties of the aerosol present in the atmosphere of the scene.

2. The computer implemented method of claim 1, wherein the properties of the aerosol comprise an extinction coefficient, an absorption coefficient, an asymmetry factor, and a single band-effective reflectance of the background in each band of a sensor acquiring the imagery.

3. The computer implemented method of claim 1, wherein the fitting process is comprised of a least square fitting process.

4. The computer implemented method of claim 3, wherein the least square fitting process is comprised of a chi-square fitting process.

5. The computer implemented method of claim 4, wherein the chi-square fitting process, for a given predefined aerosol type, comprises fitting a state space representing background reflectance for each of the multiple spectral bands and visibility to a measurement space representing the radiance measurements of the at least one calibration target and the single radiance calibration reference for the background.

6. The computer implemented method of claim 4, wherein the chi-square fitting process for a given, predefined aerosol type, comprises, determining an initial estimate for a state space defined by a gray body equivalent background reflectance in each of the multiple spectral bands, and a visibility for the scene, the background reflectance being determined by solving for the background reflectance by forward model functions mapping the background reflectance and visibility to radiance measurements of the at least one calibration target and the single radiance calibration reference for the background and the spectral reflectance of the at least one calibration target; and minimizing a chi-square penalty function for the state space, the chi-square penalty function being defined in terms of a difference between a radiance for each of the calibration targets in each of the multiple spectral bands, as determined by the forward model functions, and the measured radiances for the at least one calibration target in each of the multiple spectral bands.

7. The computer implemented method of claim 6, wherein the chi-square penalty function is minimized iteratively.

8. The computer implemented method of claim 6, wherein the forward model functions are comprised of $N_b \cdot (N_r+1)$ functions denoted $L_{i,j}: R^{N_b+1} \rightarrow R$ for $i=0, K, N_r$ and $j=0, K, N_b-1$, wherein $L_{i,j}(\rho_j, v; p_i^r)$ is defined by:

$$L_{i,j}(\rho_j, v) = \begin{cases} \int \left[ L^{AS} + \frac{\rho_i^r}{1-\rho_j S} L^{SR} + \frac{\rho_j}{1-\rho_j S} L^{BSR} \right] R_j(\lambda) d\lambda & i = 0, K, N_r-1 \\ \int \left[ L^{AS} + \frac{\rho_j}{1-\rho_j S} (L^{SR} + L^{BSR}) \right] R_j(\lambda) d\lambda & i = N_r \end{cases}$$

wherein $N_r \geq 1$ is a number of calibration targets within the imagery and $N_b$ is the number of bands of a sensor acquiring the imagery; and wherein $L^{SR} = L^{DSR} + L^{SSR}$ and $L^{BSR} = L^{BDSR} + L^{BSSR}$; $L^{AS}(\lambda)$ being solar photons that are scattered into the sensor's field of view via single or multiple scatter events within the atmosphere without ever reaching the target or background; $L^{DSR}(\lambda)$ being solar photons that pass directly through the atmosphere to a 100% reflectance Lambertian target, reflect off the target, and propagate directly through the atmosphere to a sensor that acquires the imagery; $L^{SSR}(\lambda)$ being Solar photons that are scattered by the atmosphere onto a 100% reflectance Lambertian target, reflect off the target, and propagate directly through the atmosphere to the sensor; $L^{BDSR}(\lambda)$ being solar photons that are directly transmitted to a 100% reflectance Lambertian background, reflect off the background once, and then scatter into the field of view of the sensor; $L^{BSSR}(\lambda)$ being solar photons that are scattered by the atmosphere at least once, reflect off a 100% reflectance Lambertian background once, and then scatter into the field of view of the sensor; $S(\lambda)$ being a spherical albedo of the bottom of the atmosphere, which can be thought of as a reflection coefficient of the atmosphere; and $R_j(\lambda)$ being the relative spectral response function of the sensor in band j.

9. Non-transitory computer-readable storage media, storing instructions that, when read by the computer, cause the computer to perform a method, the method comprising:

receiving multispectral or hyperspectral computer imagery of the scene, from which radiance measurements in at least two spectral bands can be obtained;

receiving a delineation within the imagery of at least one calibration target made from a known material;

determining from the imagery a radiance measurement for each target of the at least one calibration target in multiple spectral bands including each of at least two spectral bands having distinct wavelength ranges;

determining from the imagery a single radiance calibration reference for a background common to each target the at least one calibration target;

receiving for the material of which each of the at least one calibration targets, a predetermined reflectance in the multiple spectral bands, the single calibration reference excluding non-background radiance measurements from the at least one calibration target;

for each of a predefined plurality of aerosol types, each aerosol being defined by a plurality of properties, fitting a background reflectance of the scene to radiance measurements of the at least one calibration target and the single radiance calibration reference for the background, using at least the properties of the aerosol and the spectral reflectance of the at least one calibration target in each of the multiple spectral bands; and selecting the predefined aerosol that results in the best fit, the properties of the predefined aerosol being estimates for the properties of the aerosol present in the atmosphere of the scene.

10. The computer-readable storage media as set forth in claim 9, wherein the properties of the aerosol comprise an extinction coefficient, an absorption coefficient, an asymmetry factor, and a single band-effective reflectance of the background in each band of a sensor acquiring the imagery.

11. The computer-readable storage media as set forth in claim 9, wherein fitting for a given predefined aerosol type is comprised of a least square fitting.

12. The computer-readable storage media as set forth in claim 11, wherein the least square fitting process is comprised of a chi-square fitting.

13. The computer-readable storage media as set forth in claim 12, wherein the chi-square fitting process comprises fitting a state space representing background reflectance for each of the multiple spectral bands, predefined aerosol type, and visibility to a measurement space representing the radiance measurements of the at least one calibration target and the single radiance calibration reference for the background.

14. The computer-readable storage media as set forth in claim 12, wherein the chi-square fitting process comprises,
  determining an initial estimate for a state space defined by a gray body equivalent background reflectance in each of the multiple spectral bands, and a visibility for the scene, the background reflectance being determined by solving for the background reflectance by forward model functions mapping the background reflectance and visibility to radiance measurements of the at least one calibration target and the single radiance calibration reference for the background and the spectral reflectance of the at least one calibration target; and
  minimizing a chi-square penalty function for the state space, the chi-square penalty function being defined in terms of a difference between a radiance for each of the calibration targets and background in each of the multiple spectral bands, as determined by the forward model functions, and the measured radiances for the at least one calibration target and the background in each of the multiple spectral bands.

15. The computer-readable storage media as set forth in claim 14, wherein the chi-square penalty function is minimized iteratively.

16. An apparatus for estimating properties of aerosol present in the atmosphere of a scene from imagery taken of the scene, comprising:
  means for storing multispectral or hyperspectral imagery of the scene, from which radiance measurements in at least two spectral bands can be obtained;
  means for determining, in response to delineation within the imagery of at least one calibration target made from a known material and a background common to each of the at least one calibration target, from the imagery a radiance measurement for each target of the at least one calibration target in multiple spectral bands including each of at least two spectral bands having distinct wavelength ranges, and from the imagery a single radiance calibration reference for the background, the single calibration reference excluding non-background radiance measurements from the at least one calibration target;
  means for fitting, for each of a predefined plurality of aerosol types, each aerosol being defined by a plurality of properties a background reflectance of the scene to radiance measurements of the at least one calibration target and the single radiance calibration reference for the background, using at least the properties of the aerosol and, for each target of the at least one calibration target in each of the multiple spectral bands, a previously determined spectral reflectance for the material of which it is made; and
  means for selecting the predefined aerosol that results in the best fit, the properties of the predefined aerosol being estimates for the properties of the aerosol present in the atmosphere of the scene.

17. The apparatus of claim 16, wherein the properties of the aerosol comprise an extinction coefficient, an absorption coefficient, an asymmetry factor, and a single band-effective reflectance of the background in each band of a sensor acquiring the imagery.

18. The apparatus of claim 16, wherein the means for fitting is comprised of a means for least square fitting.

19. The apparatus of claim 18, wherein the means for least square fitting is comprised of means for chi-square fitting.

20. The apparatus of claim 19, wherein the means for chi-square fitting is adapted for fitting a state space representing background reflectance for each of the multiple spectral bands, predefined aerosol type, and visibility to a measurement space representing the radiance measurements of the at least one calibration target and the single radiance calibration reference for the background.

21. The apparatus of claim 19, wherein the means for chi-square fitting for a given, predefined aerosol type, comprises,
  means for determining an initial estimate for a state space defined by a gray body equivalent background reflectance in each of the multiple spectral bands, and a visibility for the scene, the background reflectance being determined by solving for the background reflectance by forward model functions mapping the background reflectance and visibility to radiance measurements of the at least one calibration target and the single radiance calibration reference for the background and the spectral reflectance of the at least one calibration target; and
  means for minimizing a chi-square penalty function for the state space, the chi-square penalty function being defined in terms of a difference between a radiance for each of the calibration targets in each of the at least two spectral bands, as determined by the forward model functions, and the measured radiances for the at least one calibration target in each of the multiple spectral bands.

22. A computer implemented method for estimating properties of aerosol present in the atmosphere of a scene from imagery taken of the scene, comprising:
  receiving with a specially programmed computer imagery of the scene, from which radiance measurements in at least two spectral bands can be obtained;
  receiving with the specially programmed computer a delineation within the imagery of at least one calibration target made from a known material;
  determining from the imagery a radiance measurement for each of the at least one calibration targets in each of at least two spectral bands;
  determining from the imagery a radiance measure for a background common to all of the at least one calibration target, but excluding the at least one calibration target;
  for each of a predefined plurality of aerosol types, each aerosol being defined by a plurality of properties, fitting with a fitting process executing on the specially programmed computer a background reflectance of the scene to the measured radiances of the at least one calibration target and the background, using at least the properties of the aerosol and a predetermined spectral reflectance of the at least one calibration target;
  selecting the predefined aerosol that results in the best fit, the properties of the predefined aerosol being estimates for the properties of the aerosol present in the atmosphere of the scene;
  wherein the fitting process is comprised of a least square fitting process, and wherein the least square fitting process is comprised of a chi-square fitting process;
  wherein the chi-square fitting process for a given, predefined aerosol type, comprises, determining an initial estimate for a state space defined by a gray body equivalent background reflectance in each of the at least two bands, and a visibility for the scene, the background reflectance being determined by solving for the background reflectance by forward model functions mapping the background reflectance and visibility to measured radiances of the at least one calibration target and the background and the spectral reflectance of the at least one calibration target; and minimizing a chi-square penalty function for the state space, the chi-square penalty function being defined in terms of a difference between a radiance for each of the calibration targets in each of the at least two bands, as determined by the forward model functions, and the measured radiances for the at least one calibration target in each of the at least two bands wherein the forward model functions are comprised of $N_b \cdot (N_r+1)$ functions denoted $L_{i,j}: R^{N_b+1} \to R$ for $i=0, K, N_r$ and $j=0, K, N_b-1$, wherein $L_{i,j}(\rho_j, v; \rho_i^r)$ is defined by:

$$L_{i,j}(\rho_j, v) = \begin{cases} \int \left[ L^{AS} + \frac{\rho_i^r}{1-\rho_j S} L^{SR} + \frac{\rho_j}{1-\rho_j S} L^{BSR} \right] R_j(\lambda) d\lambda & i = 0, K, N_r - 1 \\ \int \left[ L^{AS} + \frac{\rho_j}{1-\rho_j S} (L^{SR} + L^{BSR}) \right] R_j(\lambda) d\lambda & i = N_r \end{cases}$$

wherein $N_r \geq 1$ is a number of calibration targets within the imagery and $N_b$ is the number of bands of a sensor acquiring the imagery; and wherein $L^{SR} = L^{DSR} + L^{SSR}$ and $L^{BSR} = L^{BDSR} + L^{BSSR}$; $L^{AS}(\lambda)$ being solar photons that are scattered into the sensor's field of view via single or multiple scatter events within the atmosphere without ever reaching the target or background; $L^{DSR}(\lambda)$ being solar photons that pass directly through the atmosphere to a 100% reflectance Lambertian target, reflect off the target, and propagate directly through the atmosphere to a sensor that acquires the imagery; $L^{SSR}(\lambda)$ being Solar photons that are scattered by the atmosphere onto a 100% reflectance Lambertian target, reflect off the target, and propagate directly through the atmosphere to the sensor; $L^{BDSR}(\lambda)$ being solar photons that are directly transmitted to a 100% reflectance Lambertian background, reflect off the background once, and then scatter into the field of view of the sensor; $L^{BSSR}(\lambda)$ being solar photons that are scattered by the atmosphere at least once, reflect off a 100% reflectance Lambertian background once, and then scatter into the field of view of the sensor; $S(\lambda)$ being a spherical albedo of the bottom of the atmosphere, which can be thought of as a reflection coefficient of the atmosphere; and $R_j(\lambda)$ being the relative spectral response function of the sensor in band j.

* * * * *

UNITED STATES PATENT AND TRADEMARK OFFICE
CERTIFICATE OF CORRECTION

PATENT NO. : 8,558,884 B2
APPLICATION NO. : 13/100878
DATED : October 15, 2013
INVENTOR(S) : Ingram, Jr. et al.

It is certified that error appears in the above-identified patent and that said Letters Patent is hereby corrected as shown below:

In the Specification

In column 2, line 40, delete "basics" and insert --basic--, therefor

In column 3, line 6, before "if", insert --(--, therefor

In column 9, line 3-4 (Approx.), delete " $= 2 \sum_{i=0}^{N_r} \sum_{j=0}^{N_b-1} \frac{1}{\sigma_{L_{i,j}}^2} \frac{\partial L_{i,j}}{\partial \rho_m} \delta L_{i,j}$ " and insert -- $= 2 \sum_{i=0}^{N_r} \sum_{j=0}^{N_b-1} \frac{1}{\sigma_{\delta L_{i,j}}^2} \frac{\partial L_{i,j}}{\partial \rho_m} \delta L_{i,j}$ --, therefor In column 9, line 17-18 (Approx.), delete " $= 2 \sum_{i=0}^{N_r} \frac{1}{\sigma_{L_{i,m}}^2} \frac{\partial L_{i,m}}{\partial \rho_m} \delta L_{i,m}$ " and insert -- $= 2 \sum_{i=0}^{N_r} \frac{1}{\sigma_{\delta L_{i,m}}^2} \frac{\partial L_{i,m}}{\partial \rho_m} \delta L_{i,m}$ --, therefor In column 10, line 7-8 (Approx.), delete " $= 2 \sum_{i=0}^{N_r} \frac{1}{\sigma_{L_{i,n}}^2} \left\{ \frac{\partial^2 L_{i,n}}{\partial \rho_m \partial \rho_n} \delta L_{i,n} + \frac{\partial L_{i,n}}{\partial \rho_n} \frac{\partial L_{i,n}}{\partial \rho_m} \right\}$ " and Signed and Sealed this
Seventh Day of January, 2014

Margaret A. Focarino
*Commissioner for Patents of the United States Patent and Trademark Office*

CERTIFICATE OF CORRECTION (continued)
U.S. Pat. No. 8,558,884 B2 insert -- $= 2\sum_{i=0}^{N_r} \frac{1}{\sigma_{\delta L_{i,n}}^2} \left\{ \frac{\partial^2 L_{i,n}}{\partial \rho_m \partial \rho_n} \delta L_{i,n} + \frac{\partial L_{i,n}}{\partial \rho_n} \frac{\partial L_{i,n}}{\partial \rho_m} \right\}$ --, therefor In column 10, line 40 (Approx.), delete " $\frac{\partial^2 L_{i,n}}{\partial \rho_n^2} = \int \frac{\rho_i^I(\lambda) L^{SR}(\lambda) + L^{BSR}(\lambda)}{[1-\rho_n S(\lambda)]^3} S(\lambda) R_n(\lambda) d\lambda$ " and insert -- $\frac{\partial^2 L_{i,n}}{\partial \rho_n^2} = \int \frac{\rho_i^I(\lambda) S(\lambda) L^{SR}(\lambda) + L^{BSR}(\lambda)}{[1-\rho_n S(\lambda)]^3} S(\lambda) R_n(\lambda) d\lambda$ --, therefor In column 11, line 7, delete " $\chi_a$, " and insert -- $\chi_a^2$ , --, therefor In column 12, line 30, delete "are" and insert --or--, therefor In the Claims In column 14, line 41, in Claim 9, after "target", insert --of--, therefor In column 17, line 16, in Claim 22, delete "bands" and insert --bands;--, therefor